United States Patent [19]
Swanson

[11] Patent Number: 5,376,127
[45] Date of Patent: Dec. 27, 1994

[54] PROSTHESIS COVER AND METHOD OF PRODUCING

[76] Inventor: Vern M. Swanson, 4225 Renshaw Run, Lambertvill, Mich. 48144

[21] Appl. No.: 723,759

[22] Filed: Jul. 1, 1991

[51] Int. Cl.$^5$ ............ A61F 2/60; B29C 43/12; B29C 51/10
[52] U.S. Cl. .................. 623/27; 623/901; 264/511; 264/554; 264/571; 264/DIG. 30
[58] Field of Search ............ 623/27, 33, 901; 264/554, 571, DIG. 30, 511 (U.S. only)

[56] References Cited

U.S. PATENT DOCUMENTS

| | | | |
|---|---|---|---|
| 3,954,931 | 5/1976 | Helmuth et al. | 264/571 |
| 4,395,783 | 8/1983 | Eyre et al. | 623/27 X |
| 4,473,421 | 9/1984 | Gustafsson | 264/DIG. 30 X |
| 4,578,826 | 4/1986 | Adiletta | 264/571 X |
| 4,676,801 | 6/1987 | Lundeen | 623/53 |
| 4,696,780 | 9/1987 | Hagglund | 623/33 X |
| 4,920,580 | 5/1990 | Liff | 623/66 X |
| 4,983,341 | 1/1991 | Kromrey | 264/571 X |
| 5,007,937 | 4/1991 | Fishman et al. | 623/34 |
| 5,116,381 | 5/1992 | Palfray | 623/33 |

FOREIGN PATENT DOCUMENTS

| | | | |
|---|---|---|---|
| 2067074 | 7/1981 | United Kingdom | 623/27 |
| 0467741 | 4/1975 | U.S.S.R. | 623/27 |

*Primary Examiner*—David H. Willse
*Attorney, Agent, or Firm*—Paul F. Stutz

[57] ABSTRACT

A light-weight cover or shield, having the appearance of, and contour of, a human limb, adapted/designed to surround the endoskeletal component of a prosthesis, is provided by heating and deforming a preform composed of a closed cell polyethylene sheet material of specified thickness, to yield said contoured cover/shield of extremely light weight and being toolable for tailor finishing to individual requirements.

7 Claims, 3 Drawing Sheets

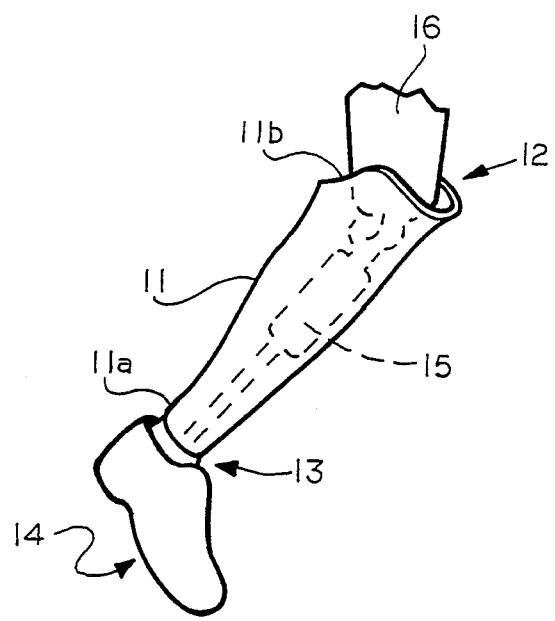
FIG. 1
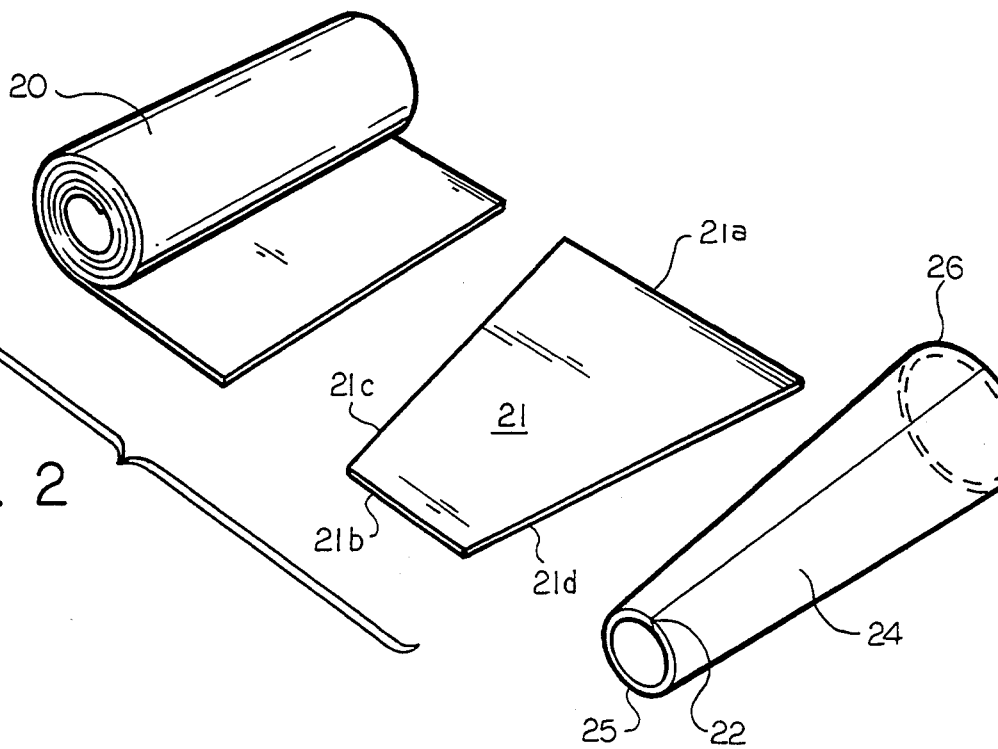
FIG. 2
FIG. 3

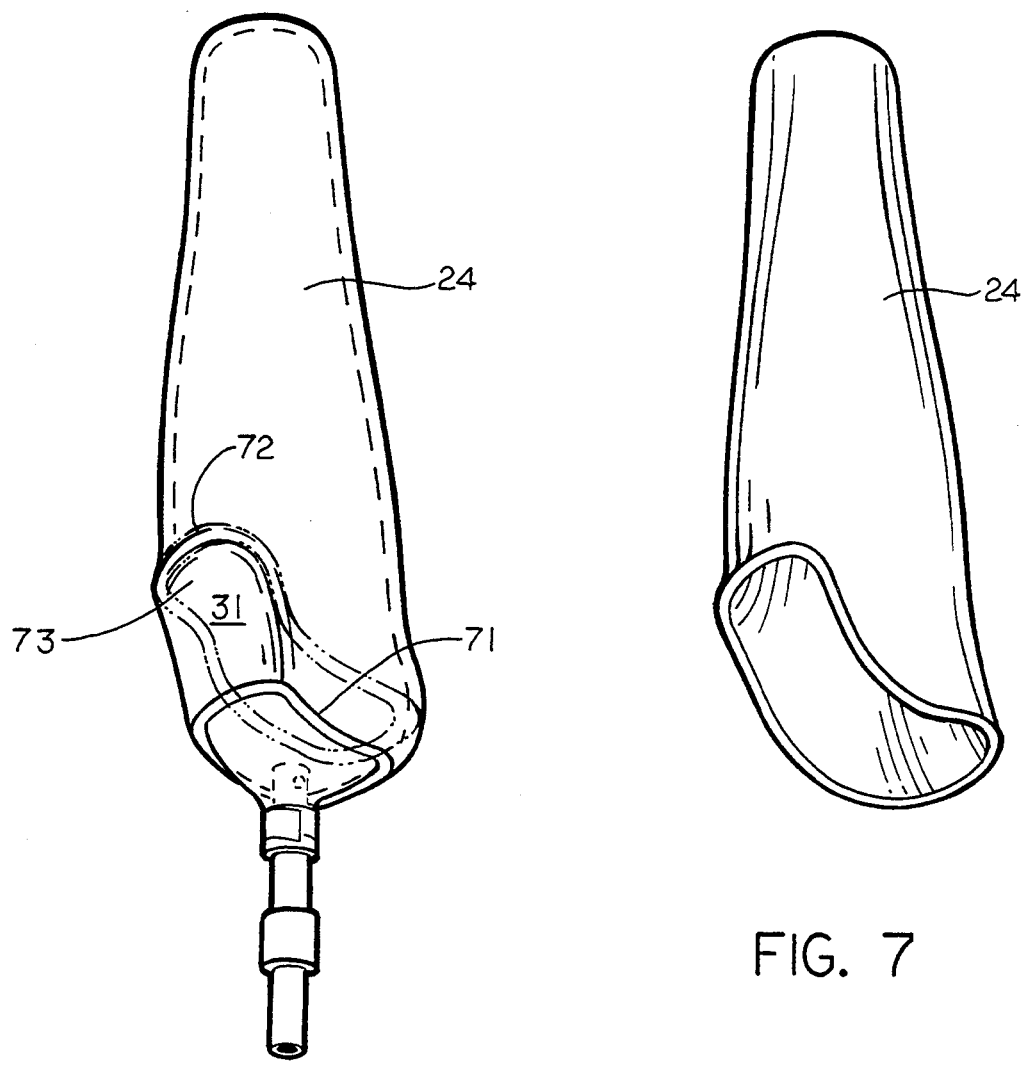
FIG. 6
FIG. 7
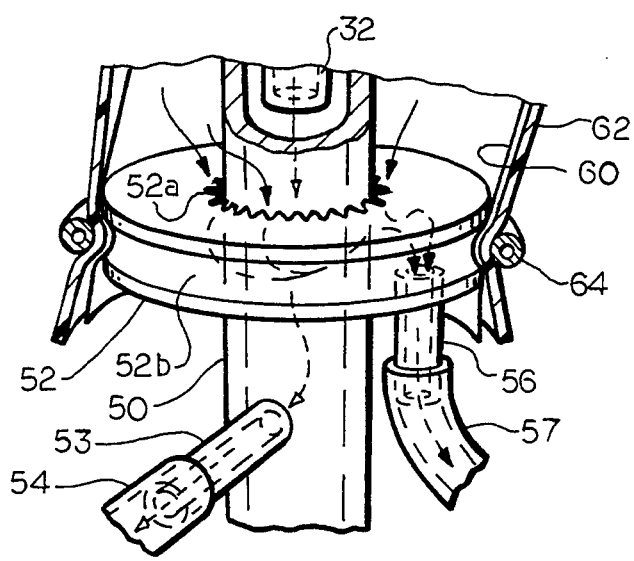
FIG. 8

PROSTHESIS COVER AND METHOD OF PRODUCING

INTRODUCTION

The present invention relates generally to the field of the production/manufacture (and of fitting) of prosthetic devices to individuals who have suffered the loss of a limb as a result of an accident, or from disease such as cancer. Even more commonly, an amputation is necessitated by impaired, destroyed or defective circulation of a persons blood supply, such that the limb extremity, to varying degrees, may no longer be effectively nourished or provided with the necessary blood conveyed components essential to health/maintenance of the particular limb.

The prosthesis to which the present invention generally relates is an artificial/substitute/replacement limb or arm or any part thereof.

In the present description/application; the ensuing discussion and disclosure will be confined to the situation wherein the artificial limb is a leg, albeit the improvement herein involved is equally applicable to the replacement/artificial arm.

BACKGROUND

The prosthesis may involve a replacement foot, ankle, and foreleg, or the latter plus a knee and a preselected length of the upper leg or femur; depending upon the needs of the particular patient/individual and the nature of the affliction requiring the prosthesis. The prosthesis may even include a hip in an extreme case.

The functional component of a prosthesis is composed of an endoskeletal system composed of metal (load bearing); elements, and usually motion imparting or permitting joints, pivots, bearings permitting turning or partial turning and flexing or partial flexing; the latter for the purpose of simulating a natural movement or gait. The endoskeletal component may also include certain rigid plastics, where their individual strengths and lightness permit their substitution for traditionally used metals of light weight, such as aluminum or titanium etc. A further important component of a prosthesis is a surrounding element or elements which mask or hide the endoskeletal component and additionally serve to simulate the appearance and contour of the missing limb.

One technique for hiding, covering, shielding or masking the structural (and/or endoskeletal) component contemplates an encapsulation of the structural components with a matrix substance formed from a liquid resin containing a blowing agent which by-/through application and control of appropriate conditions creates a foamed-in-place matrix, mass or body, which is thereafter processed by appropriate tooling and finishing to approximate the appearance/contour of the limb replaced. In a variant approach, a form or enclosure is positioned about the endoskeletal region as to define a cavity; and thence, there is introduced thereto, a volume of liquid resin containing a suitable blowing agent. Thereafter heat and/or pressure is applied to convert same to a cellular matrix which is hopefully of lower weight.

The product of the techniques as described above requires considerable time, handicraft and tooling in order to attempt to tailor make the desired cover or shield; and at the same time simulating the contour/appearance of an actual limb. Usually the resulting product is less than satisfactory because it lacks durability, is heavy, compared to the cover of the invention, and requires much more labor to install.

The foregoing also has the drawback that the foam-in-place material must be usually destroyed if the structural component, which may include hydraulic units, control units sockets etc. and possibly other elements requiring inspection, requires lubrication and/or service in any respect.

Vinyl resins such as Geon 121 manufactured by B. F. Goodrich Co. of Akron, Ohio are used in making a reshapeable prosthesis, as disclosed in U.S. Pat. No. 4,704,129. The technique of the latter patent commences with the formation of a cone from the vinyl resin ("Geon 121") via a slush cast technique employed in a heat transfer mold. The technique further employs a model about which the cone is located for reforming and resetting same to the desired configuration usually preceded by a preheating step. The final product, as described in the '129 patent, is a socket separated from the mold by the application of compressed air thru appropriately provided ports.

It is also presently conventional to prepare covers which are cellular and shaped by the expedient/technique of injection molding. In this approach a multi-cavity mold, usually fabricated of stainless steel, usually two mating plates machined to contain there between, a plurality of cavities or voids which define an elongate, open ended structure with the outer surface having the appearance of the limb in question. A liquid resin containing a suitable blowing agent is pumped into each of the voids of the multi cavity mold, which is then heated frequently thru the circulation of steam in and through internal passageways formed in the body of the mold, whereupon the resin expands due to the heat activation of the blowing agent to yield the molded (cured) product which is cellular. The piece may be entirely cylindrical, as achieved by the use of mold inserts and appropriate mold design, or the product may be a half cover which is combined with a second matching half cover and secured by suitable adhesive at the mating edges to yield a cover surrounding the endoskeletal system or structure.

While considerable uniformity and some economy is achieved by the injection molding technique; the end product has a rather rubberlike composition and is also amorphous and is quite difficult to cut and trim in order to custom fit it with complementary components of the prosthesis, for example at the ankle or at the knee or just above the knee, where the limb in question is the leg. Also use of abrasion tools; such as grinders or sanders, on the molded cover results in a very rough and cosmetically displeasing surface.

PRIOR ART

U.S. Pat. No. 3,400,408 discloses a prosthetic limb and the use of a two piece mold of aluminum surrounding the internal structural network and defining the outside shape of a leg. The mold is filled with a foam-in-place material to encase the internal skeletal structure. The surface of the foam corresponds to the desired surface of the limb by reason of the surface definition of the mold. Thereafter a thin latex covering or the like is placed over the foam material. The latex is of a color simulating that of human skin. The disclosure of this patent is representative of foam-in-place techniques.

Destruction of the foam is necessary if access to the internal structure is necessary for any reason.

The production or making of an artificial limb socket is disclosed in U.S. Pat. No. 4,307,056.

U.S. Pat. No. 3,377,416 discloses the making of a liner for an artificial limb by employing a cast-in-place technique and a semi liquid or heavy pastelike R.T.V. rubber.

U.S. Pat. No. 4,693,678 discloses an apparatus and technique for fabricating composites having a precisely contoured, smooth outer surface and a relative smooth inner surface provided by a mold arrangement which includes a rubber boot and employing a vacuum pressure, coupled with heat to form or mold the preimpregnated reinforcing material and to achieve consolidation of various layers or plies into a high strength, rigid unitary structure such as a radome used in military applications.

In summation, the state of the art, in so far as is revealed by the foregoing art, is seen as deficient in obviating the difficulties and drawbacks of presently available covers for the endoskeletal component of a prosthesis, as described earlier herein.

OBJECTS OF THE INVENTION

With the foregoing introduction, comprising a review of the back ground and the present state of the art; which manifest deficiencies, problems and general unsatisfactoriness of the present practices, it should be stated, and is stated that an overall object of the present invention is to provide an improved cover for the endoskeletal system of a prosthesis or prosthetic system and a method of making same.

It is a particular object of the present invention to provide a cover which is appreciably and significantly lighter in weight than covers presently or previously known in the art.

It is additionally an object of the present invention to provide such a cover which is extremely versatile as compared to covers presently known, or on the market, because the body, the composition, the nature of the consistency of the material are such, that it is easily and speedily adaptable and susceptible to additional processing, forming and tooling to a state, condition or configuration which is eminently compatible, functionally and cosmetically, with adjoining components of the prosthesis.

It is another object of the present invention to provide a cover which is extremely versatile in that the nature, geometry and composition of the cover, and, as well, the novel method of making/producing the cover cooperate in the fact that the cover can be produced and available in a number of standard sizes which will provide coverage of the range of individual needs or requirements without extensive modification. Further such modification, as is necessary, such as tailoring by trimming or grinding can be easily and speedily accomplished to the benefit of the patient and the technologist/fitter, of the prosthetic devices and systems.

It is a further and paramount object of the present invention to provide a method of making the above covers which is uniquely derived, delineated and designed as to enable convenient, effective and repeated reproducability as to provide, promote and ensure standardization and uniformity of the cover; all of which contribute to economy, reliability and satisfaction.

It is another object of the present invention to provide a novel method of making the improved covers which employs readily available materials, equipment, and conditions and parameters.

It is yet another object of the present invention to provide such a method of making the improved covers which embodies the advantages hereinabove and which method and advantages cooperate to define an overall system which may be readily practiced in the vast majority of existing facilities presently engaged in the practice and art of recommending and fitting a variety of prosthetic devices to the individuals in need.

The foregoing, as well as other objects of the present invention, will become readily apparent from the following detailed description of the present invention taken in conjunction with the annexed sheets of drawings, on which there are presented for purposes of illustration only, a preferred embodiment of the cover and the method of the present invention.

DRAWING DESCRIPTION

In the drawings:

FIG. 1 is a somewhat oblique, schematic view, partly in dotted line, of a partial prosthesis device, illustrating the lower leg, knee and foot.

FIG. 2 is a composite, three quarter perspective view schematically illustrating the making of a preform as one initial step of the novel method of the present invention.

FIG. 3 is a perspective view of the finished preform and a step following that illustrated in FIG. 2.

FIG. 6 is a view somewhat similar to FIG. 5 but again showing the operation at a further stage of completion.

FIG. 7 is a view like the previous FIGS. 4, 5 and 6 but illustrating the cover following completion of the preceding operative steps, and in condition for further final trimming and fitting to the individual patient.

FIG. 8 is a somewhat enlarged and detailed view, partly in section, of a portion of the apparatus illustrated near the bottom of FIG. 5, but shown somewhat enlarged in order to more clearly illustrate a feature of construction.

BRIEF DESCRIPTION OF THE INVENTION

Figure 4:
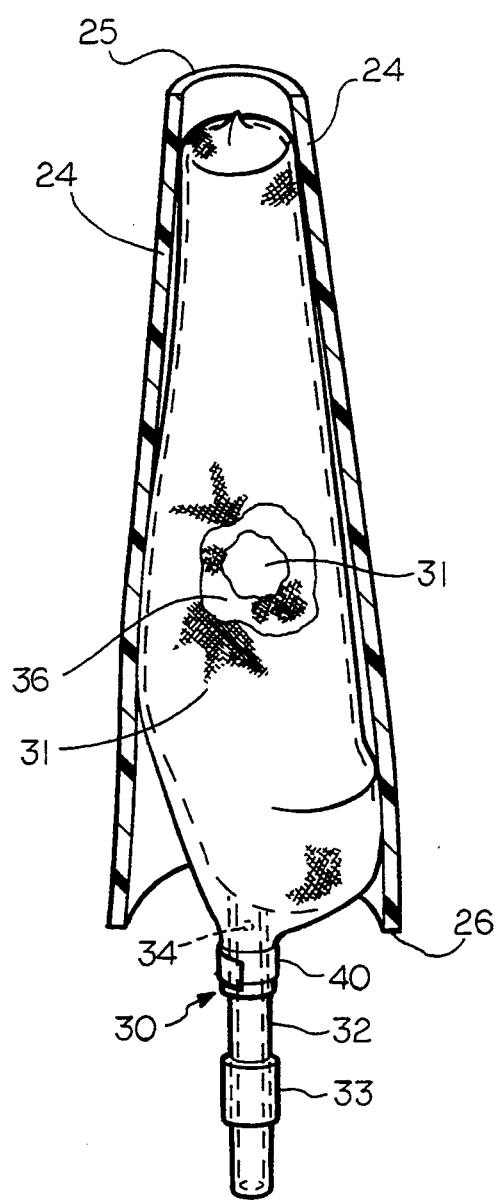
FIG. 4 is a perspective, partially sectional view, with certain components broken away in order to more readily illustrate a succeeding step of the novel method of the present invention leading to an improved cover.

The present invention contemplates the unexpected realization that a conventional and readily available cellular polyethylene sheet material could be utilized as an outer visible component of a prosthesis, serving as a cover hiding the endoskeletal system and simulating the missing limb in appearance; and, at the same time, the discovery of a novel sequence or series of operative steps which would provide for the transformation of the sheet material in planar form into a reproduceable and uniform cover uniquely adaptable for finishing to a tailored contour and dimension suitable to a wide variety of prostheses as governed by individual requirements and parameters.

DETAILED DESCRIPTION OF THE INVENTION

Referring now more specifically to the drawings, there is shown in FIG. 1 a contoured, light weight cover 11 in accordance with the present invention. The cover extends from the region of the knee designated by the reference numeral 12 to the region of the ankle designated by the numeral 13; the ankle being connected to an artificial foot 14. The cover surrounds an endoskeletal system 15 shown in dotted outline. The endoskeletal system is a combination of usually lightweight metal components employed as load bearing elements and may include pivots, bearings, hydraulic components and the like; none of which constitute a part of the present invention.

The lower end 11a of the cover has been trimmed e.g. shaped and contoured, by appropriate cutting and abrasion tooling to match, dimensionally and cosmetically, the adjoining ankle portion of the foot.

The upper end 11b of the cover 11 has likewise been trimmed to accomodate the adjoining component identified by the reference numeral 16.

Referring to FIG. 2 there is shown a roll supply 20 of foam sheet polyethylene measuring about ⅜ inch in thickness.

The polyethylene sheet material used is marketed by PEL Supply Co. 4666 Manufacturing Rd., Cleveland, Ohio; 44135 and sold under the trade name Ipoform. Ipoform is a firm density grade of lightweight foam polyethylene marketed in sheet form rolled upon itself and used frequently as an orthotic padding. Ipoform is marketed in thicknesses ranging from 5/64" to ⅜" e.g. 2 to 10 millimeters. Other polyethylene products of PEL Supply Co. are marketed under the tradenames Pelite, Aliplast, Plastazote and Ensolite. The product is made by a German concern, identified as IPOS, whose U.S. address is 2045 Niagara Falls Blvd., L.P.O. Box 320, Niagara, Falls, N.Y. 14304. PEL buys the material from IPOS and markets it in various thicknesses and shapes, usually in rolls.

In accordance with one aspect of the present invention, a length of the foam polyethylene material 21 is severed from the roll and cut into the configuration shown, having one long side 21a parallel to opposite side 21b; while the other sides 21c and 21d are angled as shown with their edges 21c and 21d angularly skived in order that they may be brought into slightly mutual over lapping relationship, as indicated by the reference numeral 22 (FIG. 3), and then adhered or knitted together by the use of an adhesive or through the application of heat. A suitable adhesive marketed under the tradename "Barge Cement", is available from Pierce & Stevens Corporation, Box 1092, located in Buffalo, N.Y. 14240, USA. The foregoing steps will yield a cone shaped preform 24 having one open end 25 approximating the circumference of an ankle, while the opposite open end 26 will approximate the circumference, in this case, of the knee region.

Referring now to FIG. 4, the numeral 30 identifies a "jig" composed of a plaster form 31 which is a reproduction of an average lower limb or leg of an individual. The plaster form or mold of the lower leg itself is not a part of the present invention. It is made or produced in a mold e.g. a female casting of an actual limb and thus closely approximates the curvilinear contour of the limb. The mold 31 is securely mounted on an upstanding hollow pipe 32 featuring, at a lower region, an annular rubber gasket 33 in surrounding relationship. The pipe also features a small transverse aperture 34 which communicates with the interior of the pipe 32 for a reason be explained hereinafter. Usually several plaster forms, of a range of sizes, are sufficient to meet varient needs.

In accordance with a preferred aspect of the present invention, the plaster mold/form 31 has telescoped over and flushly around it, a first, inner sock 36 and a second, outer sock 38, similarly in telescopic, contacting and snug relationship. The first sock is a cotton sock e.g. a rib knit stockinette having a rather large generous mesh featuring 18 ribs per inch is available from Knit-Rite, Inc. Co., 2020 Grand Avenue, P.O. Box 208, Kansas City, Mo. 64141. The outer, closed-end sock 38 is formed of "nylon" (long chain synthetic polymeric amide), elements knitted to form a mesh like structure and is available from Durr-Fillauer Medical, Inc., Orthopedic Division, 2710 Amnicola Highway, Chattanooga, Tenn., 37406. The sock 38 is smaller mesh than the cotton sock. In practice, as described, the nylon sock 38 featured about 50 ribs per inch although this could be varied considerably. The downwardly facing lower open ends of the socks are tightly secured to the pipe and taped (reference numeral 40) as shown. The jig 30 is releasably mounted on a suitable standard which will securely hold the assembly in the manner and attitude illustrated.

In accordance with the present invention the larger open end of the preform 24 is desirably telescoped downwardly and axially about the contoured mold, bearing the socks 36 and 38 and continuing until the lower edge 26 of the preform extends to the point or region indicated in the drawings leaving but a small portion of the small end of the preform extending above the top of the form/mold 31.

Before locating the preform in the manner just indicated however; the preform 24, in the approximate vertically upright, inverted position shown, is inserted in an oven thermostatically controlled to maintain a temperature of about 250° F. Retention in the closed oven is continued for a time (usually 5 minutes or so) sufficient that the preform, of the polyethylene foam material, has achieved its thermoplastic temperature, that is, that temperature at which the preform can be deformed from its cone configuration to a modified or second configuration. Thereafter upon return to room temperature (or ambient conditions) the preform will remain set to the modified or changed shape or configuration.

Figure 5:
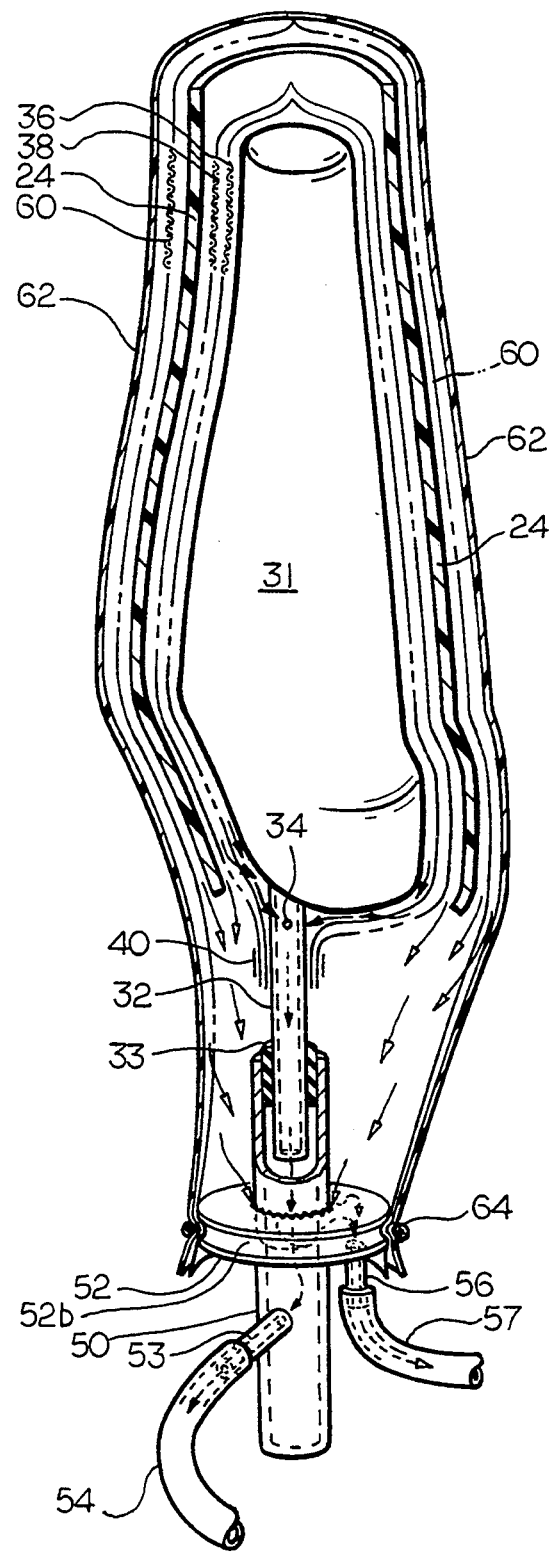
FIG. 5 is a view similar to FIG. 4, but representing the next stage, step or operation of the present invention, and with portions broken away, in order to more clearly illustrate the nature of the step and the operative conditions.

After 5 minutes or so, the preform, which is now uniformly at 250° F., is removed from the oven and telescoped down over the mold 31 bearing stockinettes (36) and (38), in the manner illustrated in FIG. 4. The assembly of FIG. 4 is now positioned, with the pipe 32 and gasket 33 inserted into the vertically held pipe, 50; all as shown in FIG. 5. The pipe 50 has an open upper end capable of receiving the pipe 32 with the gasket 33 located downwardly within the pipe 50, to create an air tight, gasket seal and which also supports the assembly in secure, vertical relationship as shown. A hollow, annular, hub-like member 52 is carried by the pipe 50 in coaxial position, as shown. The annular hub-like member features a clearance in the form of grooves 52a (see FIG. 8) at the interface with pipe 50 which extend to and communicate with the hollow interior of the hub 52. A hollow nipple 53 projects laterally from the pipe 50, likewise in fluid communication with the hollow interior of the hub, while a flexible conduit 54 telescopes axially about the nipple and is connected to a suitable source of vacuum. A second hollow nipple 56 projects downwardly from, and in communication with, the interior of the hollow hub-like member 52 and connects with a flexible tubing 57 connecting with a source a vacuum. The clearance e.g. series of grooves 52a, in the upper surface of the hub and around the pipe 50 define a passageway connecting with the interior of the hub and, in turn, in fluid communication with the hollow nipple 56 and the tubing 57 leading to the vacuum source.

In accordance with a further aspect of the present invention; with the assembly of FIG. 4 situated in the pipe 50, in the manner described and illustrated in FIG. 5; there is next telescoped about the preform 24, a closed-end, nylon mesh sock 60, and, thence, an outer plastic, air-impervious tube-like sock 62, with an open lower end generally coextensive with the lower open end of the nylon net sock 60. These lower ends are pulled tautly and downwardly to a position just beneath the hub 52 and the ends urged into engagement with the annular groove 52b and there secured with an elastic tie 64. The tie effectively creates a separate chamber defined by the plastic bag 62 and the hub 50, via the tie 64.

With an understanding gained by the foregoing description, and the illustration of FIG. 5, it will be appreciated that a vacuum imposed through the conduits 54 and 57 will be communicated to the interior of the region defined by the interior of the outer plastic tube or sock 62, in several ways. The one source of vacuum will tend to urge or evacuate air out of the interior via the clearance/grooves 52a to the interior of the hub 52, through the conduit 56 and the flexible tubing 57. The vacuum imposed through the conduit 54 will urge or evacuate air through the orfice 34 at the upper end of pipe 32, thence down through the vertical extent of the pipe 32 terminating within the pipe 50 and thence laterally out the tube 53 to conduit 54. It will be noted that the aperture 34 is situated above the tape securement 40 of inner cotton sock 36 and the nylon mesh sock 38. This arrangement will tend to exhaust air from the regions proximate the surface of the mold 31 thru and/or via the paths or voids created by the knitted mesh like socks situated between the mold and the preform, even the upper regions near the top of the overall assembly. The vacuum imposed via conduit 57 will yield an exhaustion of air through the clearance/grooves 52a at the top of the hub surrounding the pipe 50 and, by reason of the voids/paths, created by the knitted weave of the net sock 62, from the region of the assembly between the preform and the outer plastic sock.

As a result of the foregoing, the vacuum conditions at the pump, measuring in the range of 24 inches of mercury (Hg), will be quickly achieved in the entire region within and defined by the collapsing plastic bag 62. Consequently, the surrounding atmospheric pressure will uniformly and surely force the preform into firm surface contact with the mold covered snugly by the cotton sock 36 and nylon sock 38.

These vacuum conditions are continued and maintained until the temperature of the preform returns to approximate room temperature, as accelerated by the rapid movement of air in the upper regions of the assembly downwardly via the interstices present by reason of the woven nature of the layer of socks 36 and 38 on the inside of the preform and the sock 60 on the outside of the preform. Usually about 5 minutes or less is found to be sufficient. The use of forced cooling, as by fans, etc., can reduce the time for sufficient cooling to below that necessary to yield the permanent set of the preform into the shape/contour of the mold.

The return of the preform from its elevated temperature of 250° F. to about room temperature results in its taking the shape and form of the contour mold 31. This is true, both of the inner surface and the outer surface, because of the uniform thickness of the segment of the polyethylene foam material used in forming the initial cone structure placed telescopically about the mold 31.

The vacuum is imposed via the two flexible conduits 54 and 57 using a conventional vacuum pump. The one employed in the practice of the invention, as described herein, is manufactured by Dayton Electric Mfg. Co., of Chicago, Ill., 60648, (under U.S. Pat. No. 3,311,293) and can be identified as a model 4Z335 and having a capacity of 30 in. Hg.

It is salient feature of the present invention that the arrangement and assembly of components and the sequence of operations, as described, prohibits and/or precludes blockage of the free, clear and unobstructed movement of the air from the entire elongate envelope and created by the outer plastic sock 62. A suitable plastic sock is actually a tubular bag known as a PVA bag where PVA stand for polyvinyl alcohol. These closed end tubes or bags are manufactured by and available from the United States Manuf. Co., 180 N. San Gabriel Blvd., Pasadena, Calif. 91107-3488.

Desireably the bag, formed of polyvinyl alcohol, is wrapped in a cloth moistened with water for a period of 10 minutes or so before it is telescoped about the assembly as described above. The contact with water in the manner described, enhances the performance of the plastic and the handleability and movement of the bag in its telescopic application over the net covered preform, and also converts the bag to a state of higher plasticity which enhances its overall performance in the operation as described.

In the array of components, as described, it has been found that the inner cotton sock of heavy woven mesh, characterized as 18 ribs per inch serves most expeditiously in the achievement of a "wicking action"; that is the bleeding removal of air in the peripheral region surrounding the mold 31, thus causing the preform to quickly and efficiently collapse tightly into the surface abutment without the formation or presence of any bubbles or air pockets/bubbles. The latter are undesireable as they interfere with and in many cases destroy the contour of the cover such that it is unsuitable and must be rejected. At the same time it will be appreciated that it is not intended to be limited to exactly a mesh of 18 ribs per inch, since more or less will not detract from the property of providing the wicking action created by the voids and interstitial character of the structure.

The second sock 38 of nylon mesh assists in the "wicking" or bleeding of air, as just described, and, in addition, provides, in toto, a surface which permits and enhances the movement of the cone shaped preform as it is telescoped downwardly about the mold in a facile manner, rather than hindered by frictional engagement. This is particularly a factor since the preform surface, due to the cellular or foamlike surface of the sheet material, is inclined to a degree of inherent drag and resistance to the telescoping movement/arrangement absolutely necessary to the achievement of the desired result.

The outer closed end nylon sock 60 telescoped over the preform 24 is also dual functional. Thus it permits and assists in the telescoping of the outer plastic sock 62 about the preform and also leaves a peripheral void created by the netlike or meshlike structure of the woven nylon.

When the preform has cooled to about room temperature, the vacuum can be terminated. Then the tie 64 can be released, freeing the lower ends of the nylon sock 60 and the polyvinyl alcohol sock 62, whereupon these can be stripped upwardly and removed whereby the preform is exposed firmly compressed against the surface of the mold and having assumed the exact shape and contour thereof by reason of the uniform thickness of the polyethylene foam segment, as explained earlier herein.

The preform is next trimmed, via an appropriately razor sharp knife on the line 71 (see FIG. 6), along the lower region of the preform and thence on the inverted U-shaped line 72, whereby excess material can be removed leaving the void at the bottom of the preform 24, as shown in FIG. 7, and thus enabling the preform to be removed from the mold 31 despite the undercut as at 73. It will be seen that the preform 24 now has the shape, contour and configuration of the cover 11 in FIG. 1, albeit inverted, from that shown in FIG. 7.

The procedures described above have been determined to be necessary in order that there is produced on a consistant basis, covers which are possessed of the advantages which are most desirable and distinguish my covers from covers presently on the market in a significent market share. The procedure outlined has also been repeated numerous times and determined as definitive of the desireability of the sequence of steps. The selection of materials and the process conditions are likewise verified by repeated efforts as confirm the reliability thereof and the operations as described. For example, elimination of the mesh stockings between the mold and the cone shaped preform yields a less desireable cover by reason of the presence of air pockets and air bubbles which, while tolerable on the inside surface, are totally unacceptable on the outside surface due to the visibility thereof detracting from the cosmetic appearance. In addition the absence of the cotton and nylon socks would require an increase in time for the vacuum to effectively produce a reliable deformation of the cone shaped preform into the desired form. The combination of using the two inner socks between the cone shaped preform and the mold yields advantages in the "wicking" phenomenon, and, at the same time, an ease in the telescoping of the cone shaped preform onto the mold, suspected as being an attribute or property contributed by the outer nylon sock, having a lower coefficient of friction, whereby resistance to the telespcopic placement of the cone shaped preform is less as compared to the resistance achieved with only a cotton sock.

It will appreciated from the foregoing that numerous modifications and substitutions may be logically and obviously suggested and easily resorted to; all without departing from the spirit and/or scope of the present invention. However all such modifications, equivalents, substitutions, and/or minor departures from the explicit description/language employed hereinabove, are intended to be considered as included within the present invention, unless to do so would do violence to the language of the appended claims.

I claim:

1. A reproducible cellular, light weight cover for surrounding the endoskeletal component of a prosthesis, said cover being formed of a thermoplastic, cellular, polyethylene sheet material of uniform thickness originally in planar form and having been formed into hollow, open ended generally conical, configuration, and thence, by the sequential application of first sufficient heat, and secondly, pressure, to cause such open ended conical structure to assume the outer contour of an elongate mold having the approximate surface configuration of the missing limb and, finally cooled to room temperature to set and rigidify said conical structure in said-desired surface configuration.

2. A repeatable method of making quantities of a lightweight prosthesis cover for surrounding the endoskeletal component of said prosthesis, which comprises;
   (1) forming a hollow, cone-shaped preform from a sheet of cellular, foam-like polyethlene material of generally uniform thickness.
   (2) heating the preform to a temperature sufficient to convert the material to a thermoplastic state;
   (3) positioning said cone shaped preform into generally, coextensively surrounding relationship with an elongate mold having a surface contour approximating the limb to be replaced by said prosthesis;
   (4) imposing atmospheric pressure upon said preform to cause it to collapse into surface abutment with said mold and an approximation of the surface contour of the mold;
   (5) maintaining said condition until the temperature of the preform is below that of the thermoplastic state; and
   (6) removing said preform from said mold for further processing.

3. The repeatable method of making quantities of a lightweight prosthesis for surrounding the endoskeletal component of said prosthesis, which comprises
   (1) forming a hollow, open-ended, truncated cone-shaped preform of about three-eighths ($\frac{3}{8}$) inch cellular thermoplastic sheet material, said open ends of said preform being circular and one end larger than the other;
   (2) heating said preform to an elevated temperature sufficient to soften said preform to a state wherein said preform may be deformed from its cone-shape;
   (3) telescoping the larger open end of said preform downwardly about an upstanding mold, with said preform in spaced surrounding relationship with said mold, said mold including a lower vacuum port and having the general surface contour of the missing limb to be replaced by said prosthesis, said mold bearing, in surface abutment, a first flexible net-like, tubular sock which is closed at the upper end, while the open lower end is gathered around and below said vacuum port connected to means for imposing a vacuum at said port;
   (4) telescoping a second net-like tubular sock having a closed upper end in a surrounding relationship with said preform with the lower end of said second sock projecting below the lower end of said first sock in surface contact with said mold;
   (5) telescoping a flexible impervious sheet material in tubular form, having a closed upper end, downwardly in flush surrounding relationship with said second tubular sock, with its open lower end generally coextensively with said second sock;
   (6) gathering said lower ends of said second sock and said impervious tubular element together into flush mutual securement just below a second vacuum port connected to a vacuum source, all while said preform is still maintained in a temperature range of about 250° F.;

(7) energizing said vacuum source to create a region of low pressure throughout the vertical extent of said assembly and particularly on the inner and outer regions of said preform, whereby atmospheric pressure exerted on said preform will force said preform into intimate surface contact with said mold to form said preform into the contour of said mold;

(8) maintaining said vacuum until the temperature cools to a temperature that will maintain the deformed contour of said mold and, thereafter;

(9) removing said outer plastic bag, said second net sock and said preform for final trimming, at the terminal ends to match adjoining components.

4. The repeatable method of making quantities of a lightweight prosthesis cover for surrounding the endoskeletal component of said prosthesis, which comprises
   (1) selecting a preselected length of sheet material formed of a lightweight cellular thermoplastic and measuring about 5-10 millimeter in thickness, said length having opposed substantially parallel edges, the space between parallel edges proximating the length of the endoskeletal element;
   (2) cutting said length into a series of separate pieces in which the third and fourth sides are non-parallel to define a trapezoid;
   (3) forming said trapezoid into a hollow; open-ended, truncated, cone shaped preform by joining appropriate edges, said open ends of said preform being circular and one end larger than the other;
   (4) heating said preform and mold assembly to an elevated temperature sufficient to soften said preform to a state wherein said preform may be deformed from its cone shape;
   (5) telescoping the larger open end of said preform downwardly about an upstanding mold with said preform in spaced surrounding relationship with said mold, said mold having the general contour of the missing limb to be replaced by said prosthesis, said mold bearing, in surface abutment, a first, flexible, net-like, tubular sock which is closed at the upper end, while the open lower end is gathered around and below a vacuum port connected to means for imposing a vacuum at said port;
   (6) telescoping a second, net-like tubular sock having a closed upper end into surrounding relationship with said preform with the lower end of said second sock projecting below the lower end of said first sock in surface contact with said mold;
   (7) telescoping a flexible impervious sheet material in tubular form, having a closed upper end, downwardly in flush surrounding relationship with said second tubular sock, with its open lower end generally coextensive with said second sock;
   (8) gathering said lower ends of said outer second sock and said impervious tubular element together into flush mutual securement just below a second vacuum port connected to a vacuum source, all while said preform is still maintained in the temperature range of the deformation temperature of said thermoplastic;
   (9) energizing said vacuum source to create a region of low pressure throughout the vertical extent of said assembly and particularly on the inner and outer regions of said preform, whereby atmospheric pressure exerted on said preform will force said preform into intimate surface contact with said mold to form said preform into the contour of said mold;
   (10) maintaining said vacuum until the temperature cools below the deformation temperature to maintain the deformed contour of said mold and, thereafter; and
   (11) removing said outer plastic bag, said second net sock and then trimming said preform at the terminal ends whereby adjoining components match complementarily.

5. The method as claimed in claim 4, wherein said mold in step five, bears two flexible, net-like tubular socks, which are closed at the upper end, while the open lower ends are gathered around and below a vacuum port connected to means for imposing a vacuum at said port.

6. The method as claimed in claim 5, wherein the innermost of said two socks is formed of cotton while the outer is formed of nylon.

7. A repeatable method of making quantities of a light weight prosthesis cover for surrounding the endoskeletal component of said prosthesis, which comprises the following temporal sequence of steps;
   (1) forming a cone shaped preform of generally uniform thickness from a planar sheet of cellular, form polyethylene material;
   (2) heating the preform to a temperature, and for a time, sufficient to convert the material to a deformable state;
   (3) locating said heated cone-shaped preform in surrounding relationship with an elongate mold having a surface contour like the limb to be replaced by the said prosthesis;
   (4) positioning an air impervious plastic bag in surrounding relationship with said cone-shaped preform;
   (5) impressing a vacuum at a lower end of said plastic bag,
   (6) gathering said bag lower extremities into close proximity, thereby causing the impervious plastic bag to collapse due to the negative pressure therewithin and translate atmospheric pressure into a force urging said preform into snug surface abutment with said mold,
   (7) maintaining said conditions until the preform configuration is stable in a configuration substantially that of the elongate mold,
   (8) removing said preform from said elongate mold, and
   (9) repeating said steps 1 thru 8 sequentially, to produce a plurality of covers for later use.

* * * * *